(12) United States Patent
Jolma et al.

(10) Patent No.: US 8,817,172 B2
(45) Date of Patent: Aug. 26, 2014

(54) ILLUMINATION OF AN OBJECT

(75) Inventors: Ilkka Jolma, Oulu (FI); Markku Virta, Kempele (FI); Mikko Tuohimaa, Kempele (FI); Juha Lipponen, Oulu (FI)

(73) Assignee: Optomed Oy, Oulu (FI)

( * ) Notice: Subject to any disclaimer, the term of this patent is extended or adjusted under 35 U.S.C. 154(b) by 85 days.

(21) Appl. No.: 13/504,263

(22) PCT Filed: Nov. 16, 2010

(86) PCT No.: PCT/FI2010/050921
§ 371 (c)(1),
(2), (4) Date: Apr. 26, 2012

(87) PCT Pub. No.: WO2011/061393
PCT Pub. Date: May 26, 2011

(65) Prior Publication Data
US 2012/0212659 A1    Aug. 23, 2012

(30) Foreign Application Priority Data

Nov. 17, 2009   (FI) ...................................... 20096192

(51) Int. Cl.
*H04N 5/222*   (2006.01)
*A61B 3/14*    (2006.01)
*G02B 5/02*    (2006.01)
*G03B 15/14*   (2006.01)

(52) U.S. Cl.
CPC .............. *A61B 3/14* (2013.01); *G02B 5/0263* (2013.01); *G03B 15/14* (2013.01)
USPC ........... 348/370; 348/131; 348/132; 348/371; 348/373; 348/335

(58) Field of Classification Search
USPC .................. 348/131–132, 370–371, 373, 335
See application file for complete search history.

(56) References Cited

U.S. PATENT DOCUMENTS

| 4,779,973 A | 10/1988 | Miller et al. |
| 5,461,417 A | 10/1995 | White et al. |
| 5,975,700 A | 11/1999 | Koest |
| 6,275,256 B1 | 8/2001 | Olczak et al. |
| 2003/0050561 A1 | 3/2003 | Bazin et al. |
| 2010/0201943 A1 | 8/2010 | Pohjanen |

FOREIGN PATENT DOCUMENTS

| DE | 102 40 904 A1 | 3/2004 |
| JP | A-2-155106 | 6/1990 |
| JP | A-2004-302424 | 10/2004 |
| WO | WO 2004/081648 A2 | 9/2004 |
| WO | WO 2009/050339 A1 | 4/2009 |

OTHER PUBLICATIONS

Ariana, D. et al. "Integrating multispectral reflectance and fluorescence imaging for defect detection on apples," *Computers and Electronics in Agriculture*, 2006, vol. 50, pp. 148-161.
Aug. 16, 2010 Finnish Search Report issued in Finnish Patent Application No. 20096192 (with translation).
Mar. 17, 2011 International Search Report issued in International Patent Application No. PCT/FI2010/050921.

*Primary Examiner* — Antoinette Spinks
(74) *Attorney, Agent, or Firm* — Oliff PLC

(57) ABSTRACT

There is provided an improved solution for illuminating an object by means of an optical component. In use, the optical component is integrated with a hand-held camera unit. The optical component comprises a light-diffusing element. In addition, the optical component may also comprise at least one light source and an end element that directs the light to the object.

22 Claims, 3 Drawing Sheets

ILLUMINATION OF AN OBJECT

FIELD

The invention relates to illumination of an object. In particular, the invention relates to use of a light-diffusing element in the illumination of an object.

BACKGROUND

When a photograph or another picture is taken of a desired object, there is a need to illuminate said object. By means of the illumination the taken picture is of considerably better quality than a picture taken of a non-illuminated object. For instance, the contours of the object to be photographed are more distinguishable by illuminating the object.

Appropriate illumination of an object is particularly important in medicine, for instance, when eyes are examined. FIG. 1 shows a prior art solution for taking pictures of eyes 120. In photographing it is possible to take a picture of the eye surface with a purpose-made device 100. The picture is formed on the basis of how a light ray directed to the eye 120 on the optical axis 110 of a camera lens 106 in a camera unit 100 reflects back from the surface of the eye 120. In order to obtain a desired picture of the eye 120, it is important to illuminate the object. The eye 120, and possibly also the area around it, may be illuminated by an illuminating device 102.

A problem is that the pictures easily show bright reflections that typically appear in pictures taken of a spherical reflecting surface such as a cornea 126 of the eye and an iris 124 around the pupil 122. In addition, human skin may also cause undesirable reflections, when the object is illuminated by a flash light 104. Reflections of the flash light 104 may mask features that should be recorded on picture. However, it is difficult, in practice, to take pictures without the flash light 104, because the camera 100 is to be close to the object and consequently access of light from the environment to the surface of the object is strongly inhibited. In addition, it is difficult to record small features on the pictures, because it is difficult to keep the distance constant and the camera 100 will jolt easily. For examining the surface parts of the eye the doctors also use a so-called slit lamp 100, in which the camera may be connected to a table stand. This makes it possible to avoid jolts, among other things. Slit lamps are relatively large in size, and it is not easy to move them.

It is important to produce pictures of the object to be examined, in which disturbing reflections and/or jolts do not appear.

BRIEF DESCRIPTION

The object of the invention is thus to provide a device and a method such that the above-mentioned problems may be solved. The objects of the invention are achieved by an optical component, a camera unit and a method, which are characterized by what is stated in the corresponding independent claims.

The invention relates thus to the devices defined in independent claims 1 and 19.

The invention relates thus to the method defined in independent claim 20.

Preferred embodiments of the invention are disclosed in the dependent claims.

BRIEF DESCRIPTION OF THE DRAWINGS

In the following, the invention will be described in greater detail in connection with preferred embodiments, with reference to the attached drawings, in which.

DESCRIPTION OF EMBODIMENTS

The devices and the method in accordance with the embodiments of the invention may be utilized in examination cameras. Examination cameras allow, inter alia, examination of the surface parts of the eyes and the areas surrounding them in medicine. In addition, examination cameras also allow examination of skin. Further, the devices and the method in accordance with the embodiments of the invention may be utilized in the field of security in collecting biometric identification data.

Eye imaging is highly important, so that information on possibly deteriorating vision is received as early as possible. The eye is a light-sensing organ of vision. Access of light into the eye is adjusted by the iris that serves as a diaphragm, whose aperture is the pupil. Light refracting parts in the eye include a cornea, a vitreous body and a crystalline lens, i.e. the lens. Objects of small size, such as veins and subtle structural features of the iris, are to be captured in the picture from the surface of the eye. Because the features require high resolution power of the camera unit, their recording on the picture requires short distance shooting such that the object is sufficiently illuminated while the camera unit remains at a constant distance from the object.

Figure 1:
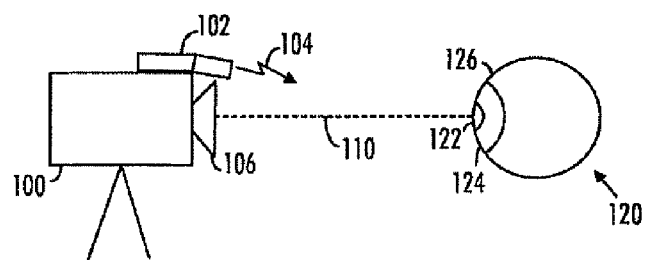
FIG. 1 shows a prior art solution for taking pictures of the eye.
Figure 2:
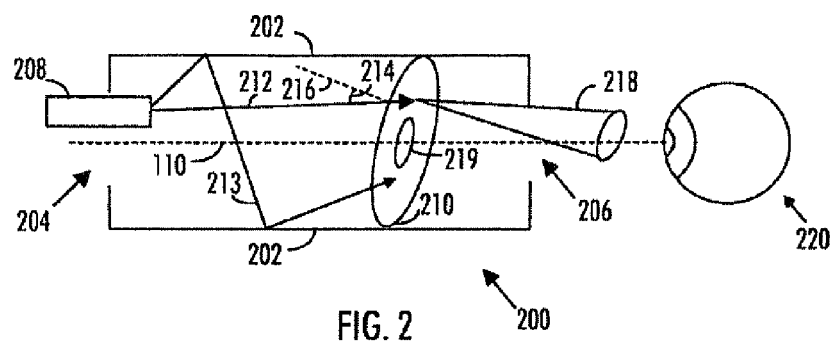
FIG. 2 shows an optical component in accordance with an embodiment of the invention.

FIG. 2 illustrates an optical component 200 in accordance with an embodiment of the invention. By means of the optical component 200 it is possible to achieve uniform, homogeneous lighting on the surface of the object 220 to be captured in the picture. In FIG. 2 the object 220 to be captured in the picture is an eye, but it could also be something else. In accordance with an embodiment of the invention, the object 220 to be captured in the picture is skin. It is important to provide uniform lighting, because in that case, for instance, the pupil of the eye will not shine as a bright spot in the picture taken of the eye.

The optical component 200 comprises a first end 204 on the side of the camera unit and a second end 206 on the side of the object to be captured in the picture. The shape of the optical component 200 may be a cylinder, a cone, a polygon, a barrel, an hourglass, a sphere, etc. Likewise, the ends 204 and 206 may be even or uneven in shape. The volume of the optical component 200 is not limited either.

The first and the second ends 204 and 206 are also free from materials obstructing the travel of light on the line of the optical axis 110 of the camera unit. This means that the first and the second ends 204 and 206 need not be open, but they may comprise a translucent material. The material shall be such that no distortions due to the material will appear in the picture to be taken. For instance, an appropriately shaped lens or glass may constitute the end 204 and/or 206.

FIG. 2 also shows that the optical component in accordance with an embodiment comprises at least one element 210 manipulating the propagation of light and consisting at least partly of light-diffusing material. According to an embodiment, the at least one element 210 is a diffuser. For the sake of simplicity, it is assumed in the specification that the optical component 200 includes the diffuser 210 that serves as the light-diffusing at least one element 210. The diffuser 210 may be arranged to diffuse the light passing through the diffuser 210 in relation to the local structural thickness of the diffuser 210 and to what is the incident angle of the light ray to the surface of the local structure of the diffuser 210. The location or the shape of the diffuser 210 is selected arbitrarily in FIG. 2 and therefore it does not restrict the shape or the location of the diffuser 210 with respect to the optical component 200. When suitably placed, the diffuser 210 could also be located outside the optical component 200.

Thus, the image taken of the object 220 and showing few or no reflections of the primary light source 208 is provided by diffusing the produced light in the optical component 200 by the diffuser 210. In that case a uniform light field is created on the surface of the object 220 to be captured in the picture.

Figure 3:
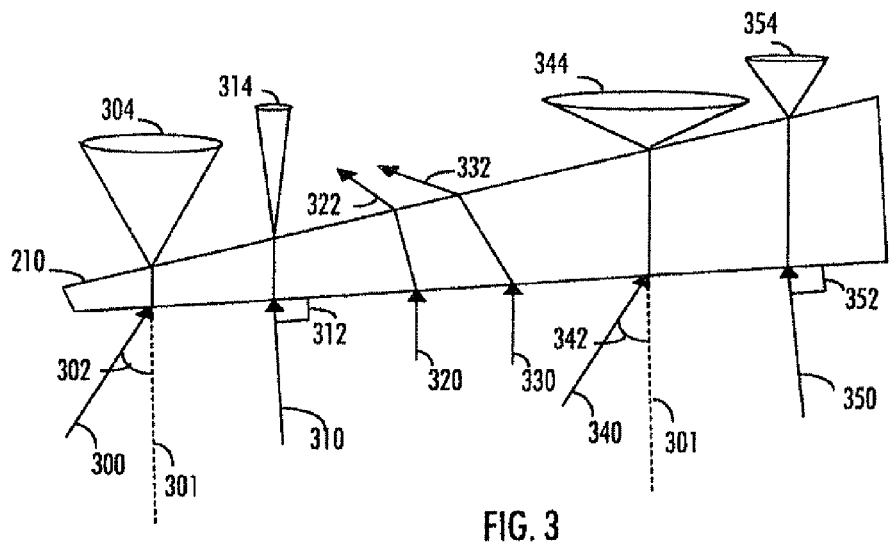
FIG. 3 shows, by way of example, how a diffuser manipulates light directed thereto.

FIG. 3 illustrates the manner how the diffuser 210 manipulates light and the travel of light. In FIG. 3, the shape of the diffuser 210 is arbitrarily chosen to make it possible to illustrate, how the thickness of the local structure of the diffuser 210 and the incident angle of the light ray 300, 310, 320, 340 and 350 to the local structure of the diffuser affect the manner how the diffuser manipulates light.

When a light ray 300 hits the normal 301 of the surface of the local structure of the diffuser 210 at an angle 302, the light 304 passing through the diffuser is more scattered than if the light ray hits the surface of the local structure of the diffuser 210 at a right angle 312 of the diffuser 210, as indicated by means of the ray 310 and transmitted light 314. In other words, the beam 304 of transmitted light is wider (light is more scattered) than the beam 314.

How the thickness of the diffuser 210 affects the light transmission of the diffuser 210 is to be illustrated with light ray pairs 300/340 and 310/350. For instance, a luminous beam 304 originating from the light ray 300 is examined and compared with the luminous beam 344 originating from the light ray 340, it is found that the beam 344 is wider than the beam 304, even though the angles 302 and 342 are equal. This results from the fact that the thicker the diffuser 210, the more it diffuses (scatters) the light transmitted therethrough. The same effect is observed in comparing the beams 314 and 354 when the light rays hit the diffuser 210 at the right angles 312 and 352. In that case it is also observed that the beam 354 is wider than the beam 314.

In short, it may be stated that the thicker the local structure of the diffuser, the more scattered the light propagated through the diffuser at said point. On the other hand, it may also be stated that the larger the angle at which the light hits the diffuser in relation to the normal of the local structure surface of the diffuser, the more scattered the light propagated through the diffuser at said point. The local structure refers to the fact that the utilized diffuser may be broader at one point than at the other. On the other hand, the surface of the utilized diffuser may also vary in shape. For instance, if the amplitude of surface roughness in the diffuser is large, two light rays coming from the same direction and hitting slightly different points in zigzag may hit at clearly different angles to the local structure of the diffuser and also to the local structures of clearly different strengths in the diffuser. It should be noted that, for the sake of simplicity, the light rays 300, 310, 340 and 350 are not intended to illustrate how a light ray is reflected in the diffuser 210, but only how incoming light is scattered while passing through the diffuser 210.

The light rays 320 and 330, in turn, illustrate how light is reflected in the diffuser 210 depending on the thickness of the local structure in the diffuser 210, even though the function of the diffuser 210 in the optical component 200 is not to reflect light, but to scatter light such that the divergence of light increases in relation to the strength of diffusion. As can be seen in the light rays 322 and 332 propagated through the diffuser 210, the thicker the structure of the diffuser, the more the light ray is reflected when passing through the diffuser 210. In reality, the luminous beams 322 and 332 would also have become wider in the diffuser 210, but in FIG. 3 this is omitted for the sake of simplicity.

Additionally, the wavelength of light used also has an effect on the reflection and scattering of light. The light of longer wavelength does not scatter or reflect as much as the light of shorter wavelength.

Light reflection and scattering properties of the diffuser 210 may be further controlled by modifying the surface of the local structure in the diffuser. An uneven surface, for instance one having high surface roughness, scatters light in a different manner than one having low surface roughness, e.g. a smooth diffuser surface.

The diffuser 210 may have a layered structure. The number of layers, constituting the local structure of the diffuser, may be two, for instance. In that case, different layers may provide different light scattering effects. For instance, one layer may be made of different material than the other, or the surface profile of one layer may be more uneven than that of the other.

Let us examine FIG. 2 more closely. The figure shows a diffuser 210 that scatters light directed thereto depending on the thickness of the local structure and on the incident angle of the light ray to the local structure. The diffuser is made of light transmitting but scattering material. In accordance with an embodiment, the diffuser consists of at least one of the following materials: polycarbonate, opalescent glass, glass and paper. The polycarbonate may be white, solid-coloured plastic, for instance. On the other hand, the diffuser 210 may be made of transparent material. For instance, the plastic diffuser 210 made of polycarbonate (PCT) may be highly durable and thus a good option. However, the material is not limited to any of the above materials, but it may be of any material that scatters light while letting light pass through. The diffuser 210 may also be partly of one material and partly of another material, and at least one of the materials shall be light-diffusing material.

In FIG. 2 an illuminator 208 is to illuminate the object 220 to be captured in the picture. In order that illumination would not generate undesirable reflections of the object 220 to be captured in the picture, the optical component 200 includes the diffuser 210, through which the illuminating light 212 travels. The shape and size of the shown diffuser 210 are arbitrarily selected. In general, a diffuser of any shape, having certain scattering properties, may be used to scatter the light directed thereto. Thus, FIG. 2 shows an arbitrarily selected, disciform diffuser 210. It should also be noted that the diffuser of FIG. 2 does not illustrate the structural thickness of the diffuser. By way of example, a light ray 212 generated by the illuminator 208 hits the diffuser at angle 214 to the normal 216 of the surface of a local structure. In passing through the diffuser 210 the light scatters and forms a luminous beam 218 that illuminates the object 220. The formed scattered light illuminates the object 220 uniformly. In that case the surface of the object becomes homogeneously illuminated. Practically no disturbing reflections will appear in the picture captured of the object 220, because illumination is not provided only by the illuminator 208, but also by the light-diffusing diffuser 210, through which the light from the illuminator 208 passes. It should be noted that the luminous beam 218 provided by the diffuser 210 of FIG. 2 is depicted by way of example only.

As stated, in an embodiment the diffuser 210 is located outside the optical component 200. In that case its location is chosen such that the light arriving at the object 220 passes through the diffuser locating outside the optical component 200. The light generated by the illuminator 208 could be conveyed by means of appropriate lenses, for instance, to the diffuser outside the optical component 200, which diffuser would diffuse the light prior to hitting the object 220.

In an embodiment part of the light is directed without diffusion to the object 220, while just part of the light passes through the diffuser 210. This solution is reasonable when pictures are taken of objects whose certain surface areas Should be provided with large amounts of light capacity without diffusion and other areas with less light intensity through diffusion so as to provide as homogeneous illumination as possible.

The colour of the diffuser 210 may also be preselected. By means of the colour it is possible to modify the visible colour from the illuminator 208 to have a specific colour. Light of different colours may be utilized in various applications and examinations. For instance, the eye may be imaged in various ways depending on the changes searched for. The structure of the eye is multi-layered depthwise, and different layers may be revealed by using light of different colours in imaging.

In accordance with an embodiment, the diffuser 210 is detachable and changeable. The user may detach the diffuser 210 from the optical component 200, choose another diffuser and mount it to the optical component 200. In that case it is possible to use the same optical component 200 for different objects 220 to be examined instead of changing the entire optical component 200. Various diffusers may be different in size, colour, material and in optical properties, etc. This feature may be utilized also when the diffuser 210 breaks down and the diffuser 210 needs to be replaced.

Moreover, FIG. 2 illustrates that, in accordance with an embodiment, the diffuser 210 is optically free 219 on the line of the optical axis 110 of the camera unit. This for the reason that, otherwise, the diffuser 210 might cause distortions in the picture taken of the object 220. The optically free point in the diffuser 210 refers to the fact that the point is free from materials disturbing the travel of light. The point 219 may be glazed, for instance, and yet allow picture taking through the glass.

In accordance with an embodiment, the optical component 200 comprises a lateral profile 202 between the ends 204 and 206. At least part of the inner surface of the lateral profile 202 is made of light-reflecting material. The lateral profile 202 may have an even or uneven surface, it may comprise apertures or it may be solid. The lateral profile 202 may extend over the first or the second end 204 and 206, if necessary. This is useful because of the fact that the light emitted from the illuminator 208 is reflected back from the inner surface of the lateral profile 202 towards the diffuser 210 instead of the part of light that hits the lateral profile 202 remaining unutilized for the illumination of the object 220. This is illustrated by a light ray 213 that is emitted from the illuminator 208 and reflected back from the inner surface of the lateral profile 202 towards the diffuser 210. For the sake of simplicity, the luminous beam produced by the diffuser 210 is not shown in the figure. The reflecting material may be e.g. a mirror, bright metal, etc.

Figure 4:
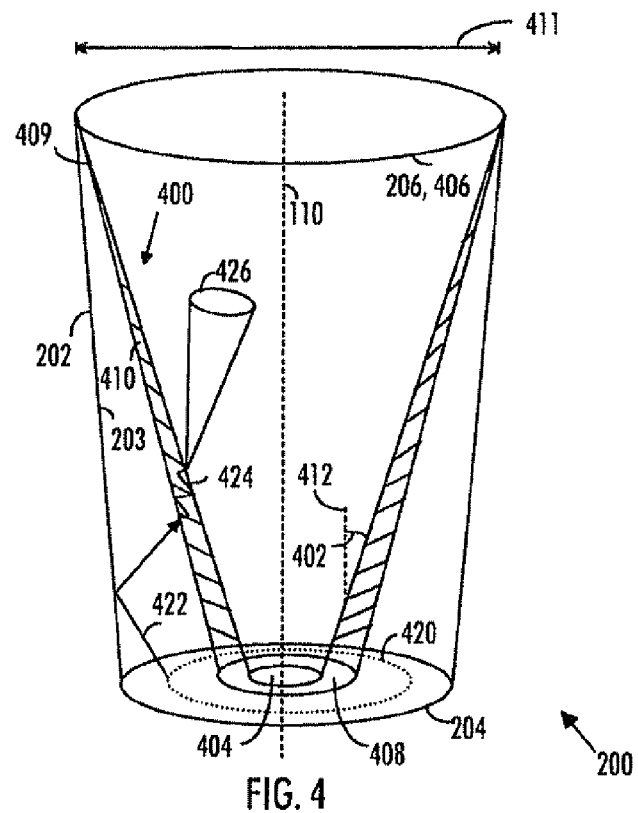
FIG. 4 shows an optical component in accordance with an embodiment of the invention.

Let us examine FIG. 4, which shows an optical component in accordance with an embodiment of the invention. In this embodiment the optical component 200 includes a diffuser, which is a truncated cone 400 in shape as shown in FIG. 4. The cone 400 may be e.g. a circular cone, a polygonal cone, an oval cone, etc. In accordance with an embodiment, the cone 400 is, however, a circular cone as is endeavoured to illustrate in FIG. 4. The cone's 400 optically free aperture 404, whose surface area is smaller, is on the side of the first end 204 of the optical component 200, and the cone's optically free aperture 406, whose surface area is larger, is on the side of the second end 206 of the optical component 200. For instance, when the cone is a circular cone, the optically free aperture of larger surface area refers to an optically free aperture of larger diameter, etc. The angle 402 of thus obtained cone's 400 lateral structure 410 to the cone's 400 central axis 412 also affects the diffusion of the light directed to the diffuser 400. In other words, the circumferential diameter 411 of the conical diffuser 400 changes in proportion to the distance from the light source 420. The diameter 411 may be varied depending on the size and other properties of the object to be captured in the picture. In an embodiment, the angle of opening (angle 402) of the conical diffuser is 0.4 to 0.5 steradians. The angle of opening is useful, inter alia, therefore that the cone 400 does not cover the frame area of the camera unit, such as camera, close to the object.

The cone's 400 apertures 404 and 406 need not be aligned with the apertures 204 and 206 of the optical component 200, even though FIG. 4 shows them that way. More precisely, the cone 400 could be shorter than the optical component 200, whereby at least one of the apertures 400 and 406 would not be in alignment with the corresponding aperture 204 and 206. In other words, at least one aperture 204 and 206 would be more in when the optical component 200 is seen in longitudinal direction, the longitudinal direction being defined by the mutual distance between the optical component apertures 204 and 206.

In FIG. 4, the conical diffuser 400 is optically free on the line of the optical axis 110 of the camera unit so that the diffuser 400 would not produce distortions in the picture taken of the object. In other words, the cone's optically free apertures 404 and 406 are in alignment with the optical axis 110 of the camera unit. The optical axis 110, even though shown to be in parallel with the lateral profile 202 of the optical component 200, may be inclined in relation to the lateral profile 202 of the optical component 200. In that case the diffuser may also be modified such that it is free from obstacles on the optical axis 110. The conical diffuser 400 need not be completely free on the line of the optical axis 110, optical transparency will suffice. Consequently, the apertures 404 and 406, or one of them, may be provided with a glass, for instance.

In the embodiment of FIG. 4, the larger aperture 406 of the cone 400 meets the inner surface 203 of the lateral profile 202 of the optical component 200. This makes it possible that light from the optical component 200 has no access to the object without the light passing through the conical diffuser 400. Said conical diffuser 400 may thus be attached to the exterior of the optical component 200.

In accordance with an embodiment, the thickness of lateral structure 410 of the cone 400 varies. Even though FIG. 4 shows that the lateral structure 410 of the cone 400 varies linearly in thickness, a change in the thickness of the lateral structure may be non-linear, for instance, uneven or barrel-shaped. For the sake of clarity, the lateral structure 410 of the cone 400 is depicted by diagonal lines in FIG. 4. Thus, the thickness of the diffuser changes in proportion to the distance from the light sources 420 so that uniform illumination is guaranteed all over the object to be captured in the picture. By changing the thickness of the diffuser the scattering of light performed by the diffuser 400 may be controlled in a desired manner. Close to at least one light source 420 it should be thicker than far from the light source 420, so that the light coming perpendicularly to the diffuser 400 may be scattered effectively.

In accordance with an embodiment, the thickness of the lateral structure 410 of the cone 400 reduces towards the larger aperture of the cone 400. As can be seen in FIG. 4, at point 408, i.e. at the end of the aperture 404 having smaller surface area, the lateral structure 410 of the cone is thicker than at point 409 at the end of the aperture 406 having larger surface area. The material thickness in the lateral structure 410 of the cone 400 may be, for instance, 3 to 5 millimetres at point 408, whereas at the other end of the conical diffuser 400 at point 409 it may be in the order of 1 mm or less.

In accordance with an embodiment, the optical component 200 may also comprise at least one light source 420 placed such that at least part of the light it produces passes through the diffuser 400 prior to hitting the object to be captured in the picture. At least one light source 420 may be located, for instance, in the manner shown in FIG. 4, at the first end 204 of the optical component 200. Alternatively, or additionally, a light source may also be located in the lateral profile 202 or within a region delimited by the lateral structure 410, the lateral profile 202 or the first end 204 of the diffuser 400, even though not shown in FIG. 4.

At least one light source 420 may be located on a purpose-made circuit board that is located at the first end 204 of the optical component 200, for instance. In use, the circuit board may communicate with the camera unit, and consequently the operation of the at least one light source on the circuit board may be controlled through the camera unit. Point 408 of the truncated end 404 of the truncated cone diffuser 400 may be located, in accordance with an embodiment, at a distance of 3 to 8 mm from the centre point of the circuit board where at least one light source 420 is located.

Alternatively, the optical component 200 need not include a light source 420. In that case the light source 420 may be in the camera unit or it may be a separate part, and as the optical component 200 in use is part of the camera unit, the light produced by the light source 420 passes through the optical component before the object to be captured in the picture. The light produced by the light source 420 that is not part of the optical component 200, is conveyed from the light source 420 to the diffuser 400, for instance, by means of photoconductors, optical fibres or lens systems. Alternatively, at the light passage point the first end 204 of the optical component 200 may be free from materials obstructing the travel of light. This point may be the same as the free point of the first end 204 on the line of the optical axis 110 of the camera unit, or it may be a different free point, whereby the first end 204 of the optical component 200 is free from materials obstructing the travel of light at least at two points: on the line of the optical axis 110 and at the passage of the light produced by at least one light source 420.

For the sake of simplicity, let us assume, however, that the optical component 200 comprises at least one light source 420 at the first end 204 in the manner shown in FIG. 4. The at least one light source may be e.g. a light emitting diode (LED), an organic LED (OLED) or another light source that may be arranged to illuminate within the VIS range of visible light. At least one light source may be a series of light sources arranged in a circle, as shown in FIG. 4, at the first end 204 of the optical component 200. In FIG. 4, each dot 420 thus represents one LED light, but the amount of dots 420 in the figure is only exemplary.

The optical component 200 may include either white or white and blue light sources, or RGB-LEDs. The light sources may be alternately on, depending on the picture-taking need. The white ones may be used in a standard picture-taking situation. The light sources producing blue light may be used, for instance, when the iris of the eye is coloured with a fluorescent colouring agent for highlighting certain features. Because of the fluorescence the colouring agent produces wavelengths of light that contribute to detection of certain features to be examined with the camera.

The optical component 200 may thus include a plurality of LED light sources and their illumination-modifying structures, such as a diffuser 210, by means of which the object is illuminated such that the object will not cause bright reflections in the picture taken of the object.

In accordance with the embodiment, the wavelength of light produced by at least one light source 420 may be predetermined. In that case it is possible to provide visible light of different colours for the illumination of the object. Light of different colours may also be utilized for various examination purposes. Accordingly, in accordance with an embodiment of the invention the light produced by at least one light source of the optical component is on a freely selectable wavelength. In addition, the light of a given wavelength scatters in a different manner in a given diffuser than the light of another wavelength. Thus, in an embodiment the wavelength of light is controlled on the basis of the object to be examined. In another embodiment, the diffuser is changed for a diffuser having specific properties on the basis of the object to be captured in the picture, while the wavelength of the light used remains the same.

In an embodiment the light provided by at least one light source is blue light the wavelength of which is within the range of 450 to 490 nanometres. This wavelength may be utilized, for instance, in examination of wounds by means of a fluorescent colouring agent. In that case, colouring agent may be applied onto the surface of the eye and it fluoresces the surface when illuminated by said wavelength. This helps to distinguish the wounds better. The blue light may also be discrete, discontinuous light.

As stated, the inner surface 203 of the lateral profile 202 of the optical component 200 may be of reflecting material, whereby the light ray 422 from at least one illuminator 420 reflects from the inner surface 203 towards the lateral structure 410 of the diffuser 400. The light ray 422 spreads in the lateral structure 410, as indicated by zigzag 424. After the diffuser 400 the light is scattered, as indicated by the light ray 426. The light ray 426 is also directed towards the object to be captured in the picture, forming uniform illumination on the surface of the object.

In an embodiment, at least one of the following: length of the lateral structure 410 of the cone 400, the angle 402 of the lateral structure 410 of the cone 400 to the central axis 412 of the cone 400 and the local thickness of the lateral structure 410 of the cone, is determined on the basis of the surface form of the object to be captured in the picture. The reason for this is that, for instance, the eye and the skin are highly different in surface forms. Consequently, it may well occur that a diffuser 400 that is well suited for one purpose is not working that well for another object to be examined. In that case the above-mentioned properties of the diffuser may have to be optimized.

As stated before, the wavelength of the light used also affects how the diffuser manipulates the travel of light. Therefore, when visible light of different wavelengths is used, the diffuser has to be optimized according to the situation. For instance, when the light of longer wavelength is used, the thickness of the lateral structure can be increased so that desired light spreading will be achieved. The properties of the diffuser 400 are determined, in addition to those mentioned above, according to the material of the diffuser 400, among other things. Therefore, when necessary, the diffuser 400 may be changed for a diffuser made of appropriate material.

Further, in accordance with an embodiment, a person skilled in the art is able, through experimentation, to find a diffuser of right shape and material for different purposes. Hence, there does not necessarily exist any table, wherefrom a diffuser of correct shape and material may be read for various purposes, but it is possible to find an optimal diffuser through empirical tests.

In accordance with an embodiment, the optical component 200 may be utilized in taking pictures of the animal eye or skin, apart from taking pictures of the human eye or skin. By varying the structure of the employed diffuser, such as the cone, the diffuser is applicable to objects of highly different sizes and shapes to be examined. By optimizing the diffuser it is possible to provide uniform illumination, for instance, for taking a picture of an animal's eye. An example of the differences between the human eye and the animal eye is the curvature of the eye. The animal eye is typically much more curved, and therefore the light must be able to illuminate uniformly, on one hand, the proximal eye part and, on the other hand, the distal eye area. Naturally, the diffuser properties required for this purpose are different from those required for the human eye. In the case of the cone diffuser 400 these properties include those mentioned above: the length of the diffuser 400, the angle 402 of the lateral structure 410, the thickness of the lateral structure 410, the colour of the diffuser 400 and the material of the diffuser 400.

Figure 5:
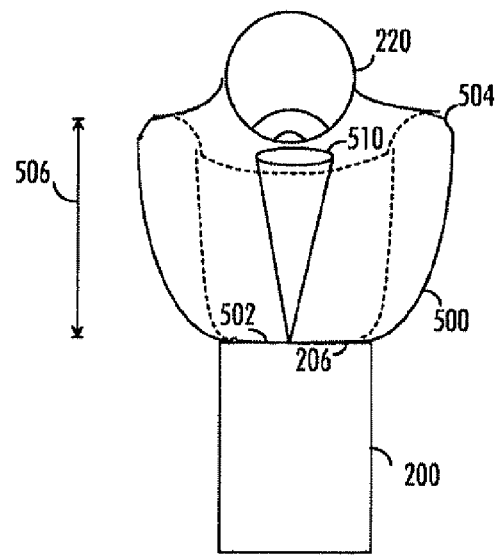
FIG. 5 shows an end element in accordance with an embodiment of the invention.

FIG. 5 shows that the optical component 200 may also comprise an end element 500. FIG. 5 is a cross-sectional view, in which the dashed lines represent contours concealed in a standard side profile view. The end element 500 is arranged to direct the light exiting from the second end 206 of the optical component 200 to the object 220 to be captured in the picture and to prevent the arrival of light to the object 220 to be captured in the picture from other directions than the optical component 200. This means that the end element 500 blocks access of light to the object to be captured in the picture, for instance, from ceiling lighting, sunlight, etc. The end element is optically hollow, whereby the light 510 from the optical element 200 has access through the end element 500 to the object 220 to be captured in the picture. Optically free means that the end element 500 may include a translucent material or substance. The shape of the end element 500 may be freely selected. For instance, it may be cylindrical. The end element 500 may be made of material that is opaque. An option for a manufacturing material is silicone.

The end element 500 may be connected to the second end 206 of the optical component 200 by means of a mechanical or a chemical connection. The connection may be located at the end 502 of the end element 500 on the side of the optical component, or it may be located on the flank of the end element 500. The end element 500 may be changed for the optical component 200 according to the object to be captured in the picture.

In accordance with an embodiment, the end element 500 being at a predetermined distance from the object 220 to be captured in the picture and coming into contact with the object 220 to be captured in the picture, the camera unit is at a focusing distance from the object to be captured in the picture 220. This predetermined distance may be determined, for instance, such that as the end element 500 comes into contact with the object to be captured in the picture 220, the camera unit is at a focusing distance from the object to be captured in the picture 220. When a picture is taken of the object 220 at the focusing distance, the picture will be sharp. Hence, the length 506 of the end element is determined such that the camera unit is at the focusing distance from the object to be captured in the picture 220, when the end element 500 connected to the optical component 200, which is attached to the camera unit, comes into contact with the object to be captured in the picture 220. In other words, the optical component 200 may comprise a mechanical part (end element 500), with which the camera is supported to the patient's head so that the imaging distance remains constant, allowing the camera to take pictures that are both steady and in focus. Thus the optical component 200 permits capturing pictures of an object to be examined by supporting the camera to the object to be captured in the picture at a constant distance.

In accordance with an embodiment, the end 504 of the end element 500 on the side of the object to be captured in the picture 220 is arranged to adapt to the contours of the object 220. The end 504 may be of adaptable material, such as soft silicone, which on pressing against the surface of the object to be captured in the picture 220 provides a close contact to the surface.

Alternatively, the end 504 of the end element 500 on the side of the object to be captured in the picture 220 is modified on the basis of the contours of the object to be captured in the picture 220. In that case, first is examined what kind of surface the object to be captured in the picture 220 has and on the basis of that information is selected the end element 500 which is able to provide a close contact to the surface.

Figure 6:
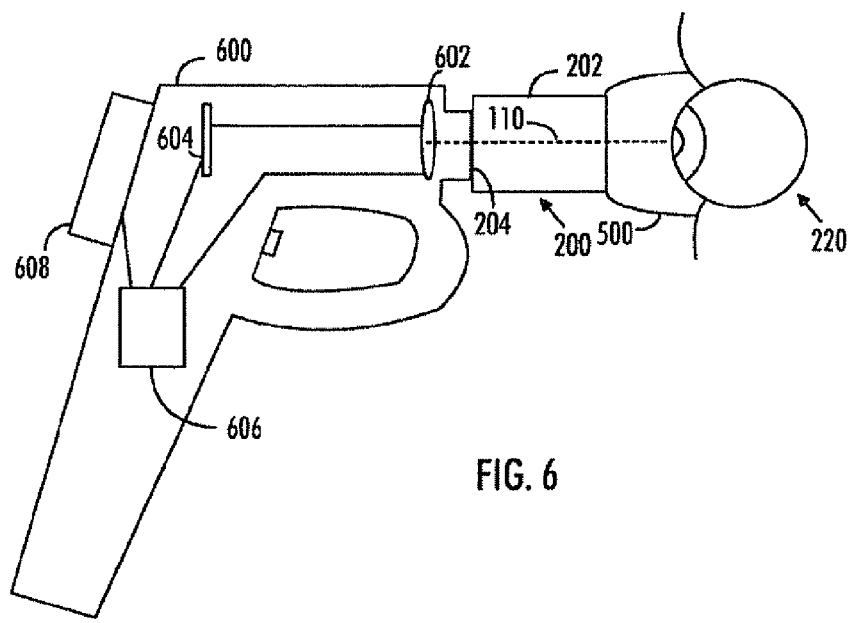
FIG. 6 shows a camera unit in accordance with an embodiment of the invention.

FIG. 6 shows a camera unit 600 in accordance with an embodiment. The examination device of this example is the camera unit 600, which may be a portable camera based on digital technology. The camera unit 600 may comprise an objective 602 having a specific optical axis 110 and allowing generation of a picture of an organ on a detector 604 of the camera unit 600. When the examination device is in the operating condition, the detector 604 may produce a picture of an organ. The picture produced by the detector 604 may be fed to a controller 606 of the camera unit 600, which controller may comprise a processor and memory for controlling the camera unit 600 and for processing and storing the picture and other optional data. From the controller 606 the picture may be fed to a display 608 of the camera unit 600 for displaying the picture and other optional data. The detector 604 of the camera unit 600 may be a CCD (Charge Coupled Device) cell or a CMOS (Complementary Metal Oxide Semiconductor) cell and the camera unit 600 may produce still pictures or video image. The images may be transferred on a data transmission connection to a computer or another desired device.

In accordance with an embodiment the optical component 200 is integrated in use with a hand-held camera unit 600. In use the integrated optical component 200 may refer to an optical component that may be integrated with the camera unit by connecting the optical component 200 to the camera unit. Alternatively, in use the integrated optical component 200 may refer to an optical component 200 that is an integral part of the camera unit, whereby it is naturally integrated with the camera unit. In other words, the optical component 200 need not necessarily be modular, but is may be part of the camera unit.

It is also possible to connect the optical component 200 to a larger camera unit, but in accordance with the embodiment its size is such that it may also be connected to a smaller, hand-held and portable camera unit. The connection may be a mechanical connection, whereby the optical component 200 may be attached to the camera unit by means of a mechanical locking mechanism. The mechanical locking mechanism may be located, for instance, in the lateral profile 202 of the optical component 200 or at the first end 204 of the optical component 200. The parts enabling the mechanical connection may be made of aluminium, for instance.

It is useful that the optical component is connectable to a hand-held camera unit or, more precisely, is integrated, in use, with a hand-held camera unit so that pictures may be taken of organs of large animals without having to lock the animal to a given position. The hand-held camera unit enables better mobility compared to a large camera and a table stand (such as slit lamp). Moreover, the hand-held and portable camera unit is practical.

FIG. 6 also shows the end element 500 and the object to be captured in the picture 220. The size of the end element 500 may be determined such that when it comes into contact with the object to be captured in the picture, the camera unit 600 is at a focusing distance from the object 220.

In addition to the camera unit 600 the examination device may comprise another, at least one modular part that is connectable to the camera unit 600. Each of these modular parts is intended for taking a picture of a predetermined organ. Thus, in addition to the optical component 200, it is possible to change a modular part to suit the object to be examined in the camera unit 600. One modular part may comprise optical elements, such as lenses and mirrors, for instance for taking pictures of the eye whereas another modular part may be designed for taking pictures of the skin. In that case there is no need to change the entire camera unit 600 when the object to be captured in the picture 220 changes, only the change of the modular part will suffice. The modular part may be placed between the camera unit 600 and the optical component 200, for instance. For the sake of simplicity, these optional modular parts are not shown in FIG. 6.

Figure 7:
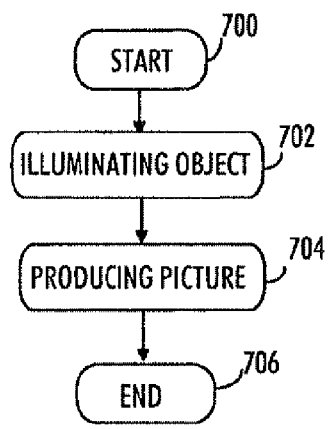
FIG. 7 is a flowchart of a method for producing an image in accordance with an embodiment of the invention.

FIG. 7 shows a method for producing a picture in accordance with an embodiment of the invention. The method starts at point 700. At point 702 the object is illuminated by utilizing an optical component in the illumination of the object. At point 704 a picture of the object is provided by the camera unit. The method ends at point 706.

It is apparent to a person skilled in the art that as technology advances the basic idea of the invention may be implemented in a variety of ways. Thus, the invention and the embodiments thereof are not restricted to the above-described examples, but they may vary within the scope of the claims.

The invention claimed is:

1. An optical component that is for uniform illumination of an object to be captured in a picture and that is integrated with a hand-held camera unit, the optical component comprising:
   a first end on a side of the camera unit and a second end on a side of the object to be captured in the picture, the first and the second ends being free of materials obstructing travel of light on a line of an optical axis of the camera unit; and
   at least one element configured to manipulate the propagation of light and made of at least partly light-diffusing material,
      the at least one element being arranged to diffuse light passing through the element and scatter the light based on (i) a local thickness of the element where the light passes through the element and (ii) an incident angle of a light ray of the light to a surface of the element where the light hits the element such that the thicker the local thickness of the element and the larger the incident angle of the light ray to the surface of the element, the more scattered the light is,
      the element forming a truncated cone such that the cone includes (i) a first optically free aperture, with a relatively smaller surface area, on a side of the element that is on the first end of the optical component, and (ii) a second optically free aperture, with a relatively larger surface area, on a side of the element that is on the second end of the optical component, wherein the thickness of a lateral structure of the cone varies along the length of the cone, and
      the first and second optically free apertures are on the line of the optical axis of the camera unit.

2. The optical component of claim 1, wherein the optical component further comprises a lateral profile between the first end and the second end such that at least part of an inner surface of the lateral profile is of light-reflecting material.

3. The optical component of claim 1, wherein the at least one element is optically free on the line of the optical axis of the camera unit.

4. The optical component of claim 1, wherein the second optically free aperture meets an inner surface of a lateral profile of the optical component.

5. The optical component of claim 1, wherein the thickness of the lateral structure of the cone reduces towards the second optically free aperture.

6. The optical component of claim 1, wherein at least one of (i) the length of the lateral structure of the cone, (ii) an angle of the lateral structure of the cone to a central axis of the cone, and (iii) the local thickness of the lateral structure of the cone is determined on the basis of a surface form of the object to be captured in the picture.

7. The optical component of claim 1, wherein the cone is a truncated, circular cone.

8. The optical component of claim 1, wherein the object to be captured in the picture is an animal eye or skin.

9. The optical component of claim 1, wherein the at least one element includes a preselected color.

10. The optical component of claim 1, wherein the at least one element is configured to be detached from the optical component and replaced with a second element.

11. The optical component of claim 1, wherein the at least one element is made of at least one of the following materials: polycarbonate, opalescent glass, glass and paper.

12. The optical component of claim 1, wherein the optical component further comprises:
   at least one light source configured to produce light such that at least part of the light from the light source passes through the element prior to hitting the object to be captured in the picture.

13. The optical component of claim 12, wherein the light from the light source is blue light and the wavelength of the light from the light source is within the range of 450 to 490 nanometres.

14. The optical component of claim 1, wherein the optical component further comprises:
   an end element arranged to (i) direct light exiting from the second end of the optical component to the object to be captured in the picture and to (ii) prevent the arrival of light to the object to be captured in the picture from directions other than from the optical component.

15. The optical component of claim 14, wherein the size of the end element is selected such that the camera unit is at a focusing distance from the object to be captured in the picture.

16. The optical component of claim 14, wherein the end element is made of silicone.

17. The optical component of claim 14, wherein an end of the end element on the side of the object to be captured in the picture is arranged to adapt to surface forms of the object to be captured in the picture.

18. The optical component of claim 14, wherein an end of the end element on the side of the object to be captured in the picture is configured to be modified on the basis of surface forms of the object to be captured in the picture.

19. A hand-held camera unit that arranged to produce a picture of an object to be captured in the picture,
wherein the optical component of claim 1 is integrated with the camera unit.

20. A method for producing a picture of an object to be captured in the picture, the method comprising:
using the optical component of claim 1 in the illumination of the object: and
producing the picture of the object with the camera unit.

21. The optical component of claim 1, wherein the cone is disposed such that the light passes through an entire width of the lateral structure of the cone.

22. The optical component of claim 1, wherein the thickness of the lateral structure of the cone varies in proportion to a distance from a light source.

\* \* \* \* \*